US012653716B2

(12) United States Patent
Quinn et al.

(10) Patent No.: US 12,653,716 B2
(45) Date of Patent: Jun. 16, 2026

(54) METHOD FOR LOCATING VISUAL AXIS FOR LASER ASSISTED OPHTHALMIC PROCEDURE WITHOUT CORNEAL MARKING

(71) Applicant: AMO Development, LLC, Irvine, CA (US)

(72) Inventors: Aaron Quinn, San Leandro, CA (US); Reena Pathania, Fremont, CA (US); Hong Fu, Pleasanton, CA (US); Daryl Wong, San Jose, CA (US)

(73) Assignee: AMO DEVELOPMENT, LLC, Irvine, CA (US)

( * ) Notice: Subject to any disclaimer, the term of this patent is extended or adjusted under 35 U.S.C. 154(b) by 439 days.

(21) Appl. No.: 18/190,061

(22) Filed: Mar. 24, 2023

(65) Prior Publication Data

US 2024/0315873 A1 Sep. 26, 2024

(51) Int. Cl.
*A61F 9/008* (2006.01)
*A61B 3/15* (2006.01)

(52) U.S. Cl.
CPC ............... *A61F 9/008* (2013.01); *A61B 3/152* (2013.01); *A61F 2009/00872* (2013.01); *A61F 2009/00878* (2013.01)

(58) Field of Classification Search
CPC ............ A61F 2009/00872; A61F 9/008; A61F 9/00827; A61F 9/009; A61F 2009/00846; A61F 2009/00897; A61F 2009/00851; A61F 2009/00882; A61F 9/0084; A61B 3/102; A61B 3/107; A61B 3/152; A61B 18/20; A61B 2017/00216; A61B 2034/107; A61B 2090/373; A61B 2090/3735; A61B 2090/3937; A61B 3/0083; A61B 3/1005; A61B 3/112; A61B 3/113; A61B 3/14; A61B 34/10; A61B 34/25; A61B 5/0073; A61B 90/361; A61N 5/067
See application file for complete search history.

(56) References Cited

U.S. PATENT DOCUMENTS

| | | | |
|---|---|---|---|
| 10,195,084 B2 | 2/2019 | Seiler et al. | |
| 10,314,745 B2 | 6/2019 | Bor | |
| 10,406,380 B2 | 9/2019 | Kurtz et al. | |
| 11,076,756 B2 | 8/2021 | Frey | |
| 11,135,093 B2 | 10/2021 | Loerner et al. | |

(Continued)

FOREIGN PATENT DOCUMENTS

| | | |
|---|---|---|
| WO | 2021048116 A1 | 3/2021 |
| WO | 2022078998 A1 | 4/2022 |

*Primary Examiner* — Deborah L Malamud

(57) ABSTRACT

A method used in a corneal lenticule procedure for finding the visual axis location before eye docking, to track the visual axis location displacement during docking, and to center the lenticule incision pattern at the visual axis location after docking, without ink-marking the visual axis location at the center of the cornea with ink or other substance. Two docking illumination beams are illuminated on the eye surface at oblique angles, and a first eye image is taken before docking while the eye looks at the fixation light of the laser system. A second eye image is taken after docking. The pre-docking cornea apex position is obtained based on the two reflected light spots of the docking illumination light. Pupil center is obtained in both images. The post-docking corneal apex is then calculated from the pre-docking cornea apex position and the pre- and post-docking pupil center positions.

20 Claims, 4 Drawing Sheets

(56) References Cited

U.S. PATENT DOCUMENTS

| | | | |
|---|---|---|---|
| 11,278,451 | B2 | 3/2022 | Andrews et al. |
| 11,419,764 | B2 | 8/2022 | Rathjen |
| 11,439,535 | B2 | 9/2022 | Rathjen |
| 2011/0224657 | A1 | 9/2011 | Stevens et al. |
| 2015/0335479 | A1 | 11/2015 | Shibata et al. |
| 2018/0008461 | A1 | 1/2018 | Fu et al. |
| 2019/0247233 | A1 | 8/2019 | Schmid et al. |
| 2021/0169691 | A1 | 6/2021 | Arba-Mosquera et al. |
| 2021/0169692 | A1 | 6/2021 | Arba-Mosquera et al. |
| 2021/0401622 | A1 | 12/2021 | Rathjen et al. |
| 2022/0062034 | A1 | 3/2022 | Abraham |
| 2022/0062039 | A1 | 3/2022 | Abraham et al. |
| 2022/0183885 | A1 | 6/2022 | Bor et al. |
| 2022/0183888 | A1 | 6/2022 | Abraham et al. |
| 2022/0387219 | A1 | 12/2022 | Scott et al. |

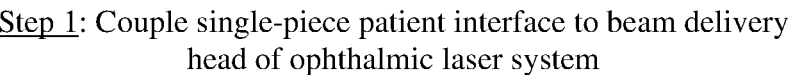

Step 1: Couple single-piece patient interface to beam delivery head of ophthalmic laser system

↓

Step 2: Lower beam delivery head with single-piece patient interface installed thereon close to but not yet in contact with patient's eye; instruct patient to look at fixation light through patient interface

↓

Step 3: Direct two oblique docking illumination light beams at eye; take first image of eye; obtain from first image: a) cornea apex location (XA, YA) which is at the center between two spots of docking illumination light beams; and b) pupil center location (XB, YB) obtained by fitting pupil edge to a circle

↓

Step 4: Further lower beam delivery head until the applanation lens contact eye surface; apply suction to couple eye to patient interface

↓

Step 5: Take second image of eye; obtain post-docking pupil center location (XB',YB') by fitting pupil edge to a circle; calculate vector difference between pupil center before and after docking, (XB'-XB, YB'-YB); calculate post-docking cornea apex location:
$$(XA', YA') = (\gamma*XA + XB'-\gamma*XB, \gamma*YA+YB'-\gamma*YB)$$

↓

Step 6: Center lenticule incision pattern at post-docking apex location; perform lenticule incisions based on centered incision pattern

Fig. 2

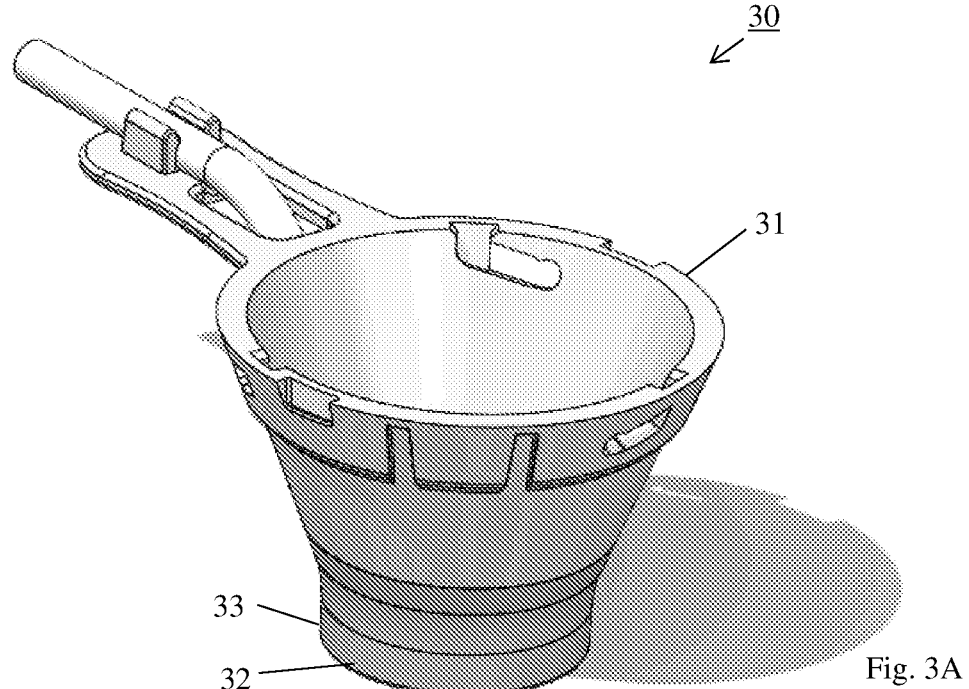
30
31
33
32
Fig. 3A
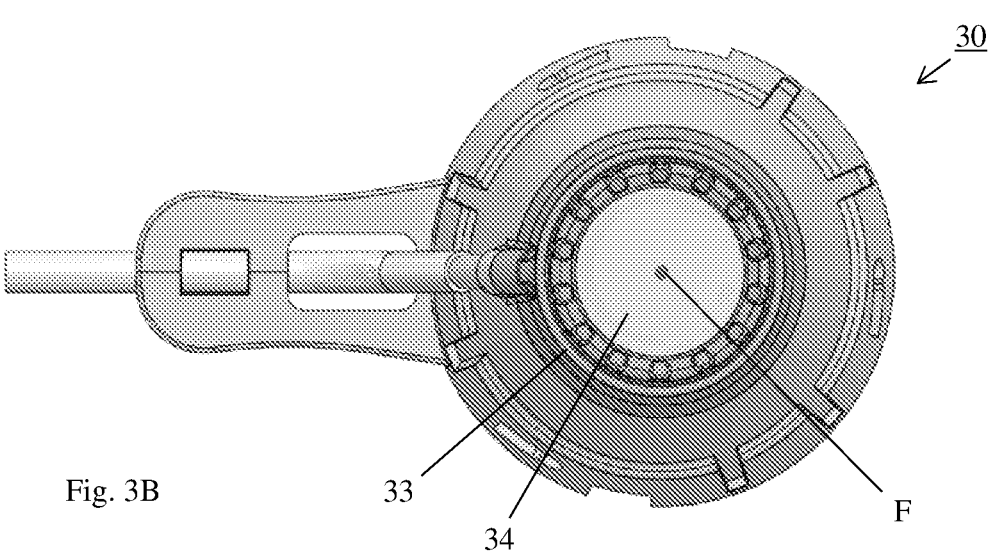
30
Fig. 3B       33
34
F

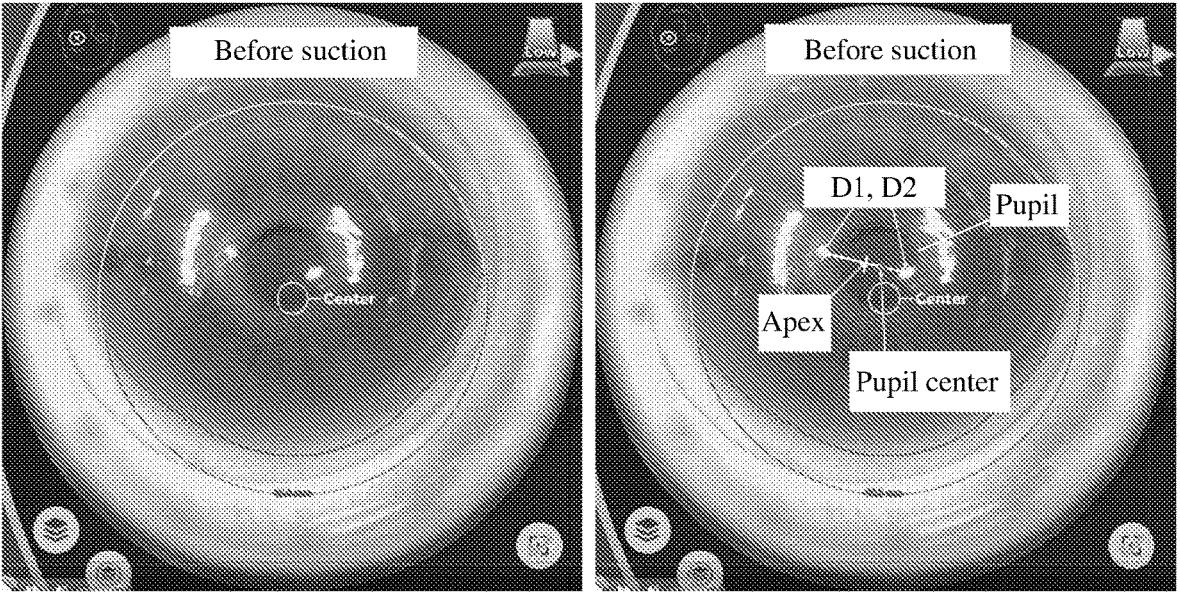
Fig. 5A
Fig. 5B
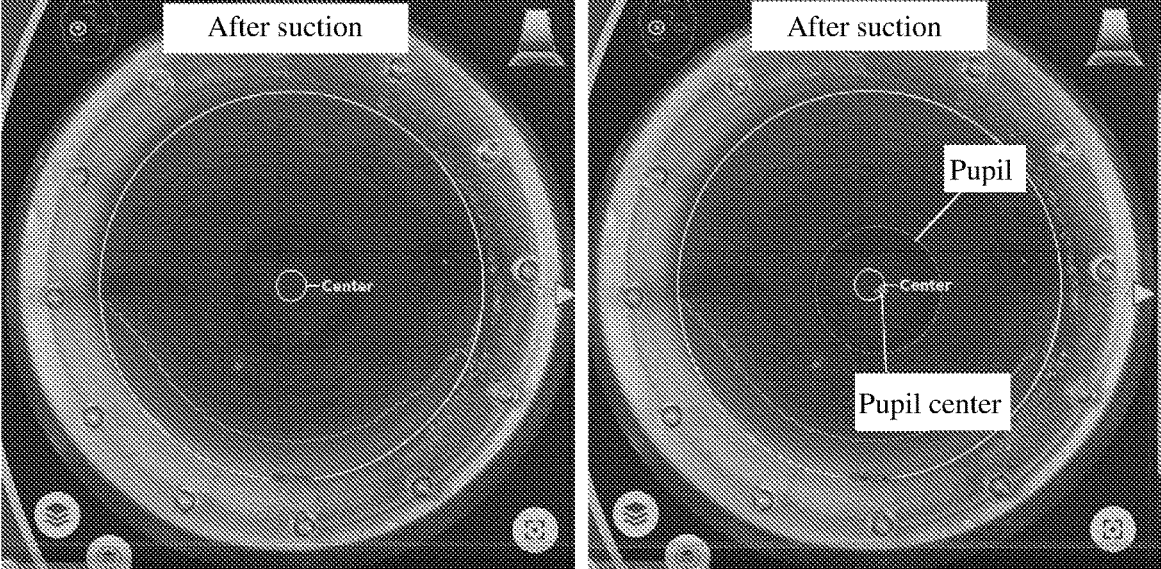
Fig. 5C
Fig. 5D

METHOD FOR LOCATING VISUAL AXIS FOR LASER ASSISTED OPHTHALMIC PROCEDURE WITHOUT CORNEAL MARKING

BACKGROUND OF THE INVENTION

Field of the Invention. This invention relates generally to laser-assisted ophthalmic procedures, and in particular, it relates to a method of locating a visual axis (cornea apex) of a patient's eye for ophthalmic laser surgery such as corneal lenticule extraction, without marking the cornea.

With recent developments in laser technology, laser surgery is becoming the technique of choice for ophthalmic procedures for vision correction. Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

In particular, since introduction of the femtosecond lasers in ophthalmology, these lasers have been extensively used in the femtosecond laser-assisted in situ keratomileusis (FS-LASIK) refractive procedures to treat myopia and astigmatism, and in the laser-assisted cataract surgeries. Superior precision and reproducibility in performing cataract anterior capsulotomy and lens fragmentation and in the lamellar flap creation are among the main advantages of the femtosecond lasers as compared to the mechanical techniques. Short pulse duration and high repetition rate of the femtosecond lasers enable application of lower levels of energy than the ones with the picosecond and nanosecond lasers in creation of the laser-induced plasma and cavitation bubbles required for tissue photo-dissection. Lower pulse energy combined with low absorption of the laser light by tissue within near infrared wavelength range significantly reduces the thermal effects and collateral damage to the neighboring tissue in femtosecond laser-assisted ophthalmic procedures.

Surgical approaches for reshaping the cornea include laser assisted in situ keratomileusis (LASIK), photorefractive keratectomy (PRK) and corneal lenticule extraction. In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In a corneal lenticule extraction procedure, instead of ablating corneal tissue with an excimer laser following the creation of a corneal flap, the technique involves tissue removal with two or more femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

In ophthalmic laser surgeries such as femtosecond laser corneal lenticule procedures, it is important to center the incision pattern at the visual axis of the patient's eye. Decentration of the lenticule (e.g., by more than 300 μm) can reduce the quality of vision.

SUMMARY OF THE INVENTION

The present invention is directed to a method and related apparatus of locating the visual axes of the cornea that substantially obviates one or more of the problems due to limitations and disadvantages of the related art.

An object of the present invention is to locate the visual axes for a corneal lenticule extraction procedure without marking the cornea with ink.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method for locating a cornea apex of a patient's eye using an ophthalmic laser system, which includes: (a) coupling a patient interface device to the ophthalmic laser system; (b) positioning the patient's eye and the patient interface device relative to each other such that the eye is below the patient interface device within a predefined distance range, without coupling the patient interface to the eye; (c) generating a fixation light which exits the ophthalmic laser system along an optical axis of the ophthalmic laser system; (d) generating one or more docking illumination beams, each of the one or more docking illumination beams exiting the ophthalmic laser system in a direction which has a predefined spatial relationship with the optical axis of the ophthalmic laser system; (e) while the eye is not coupled to the patient interface device, the eye is looking through the patient interface device at the fixation light, and the one or more docking illumination beams are incident on the eye, obtaining a first image of the eye; (f) coupling the patient interface device to the eye; (g) obtaining a second image of the eye while the patient interface device is coupled to the eye; (h) based on the first image, identifying positions of one or more light spots representing reflected light of the one or more docking illumination beams, and calculating a pre-docking cornea apex location based on the positions of the one or more light spots; (i) based on the first image, identifying a pupil of the eye and calculating a pre-docking pupil center location; (j) based on the second image, identifying a pupil of the eye and calculating a post-docking pupil center location; and (k) calculating a post-docking cornea apex location based on the pre-docking cornea apex location, the pre-docking pupil center location, and the post-docking pupil center location.

In another aspect, the present invention provides a method implemented in an ophthalmic laser system for locating a cornea apex of a patient's eye, which includes: (a) by a fixation light source of the ophthalmic laser system, generating a fixation light which exits the ophthalmic laser system along an optical axis of the ophthalmic laser system; (b) by one or more docking illumination light sources of the ophthalmic laser system, generating one or more respective docking illumination beams, each of the one or more docking illumination beams exiting the ophthalmic laser system in a direction which has a predefined spatial relationship with the optical axis of the ophthalmic laser system; (c) while a patient interface device is coupled to the ophthalmic laser system, the eye is positioned below the patient interface within a predefined distance range, the eye is looking through the patient interface device at the fixation light, and the one or more docking illumination beams are incident on the eye, obtaining a first image of the eye by a camera of the ophthalmic laser system; (d) after the patient interface is coupled to the eye, obtaining a second image of the eye by the camera; and by a controller of the ophthalmic laser system: (e) based on the first image, identifying positions of one or more light spots representing reflected light of the one or more docking illumination beams, and calculating a pre-docking cornea apex location based on the positions of the one or more light spots; (f) based on the first image, identifying a pupil of the eye and calculating a pre-docking pupil center location; (g) based on the second image, identifying a pupil of the eye and calculating a post-docking pupil center location; and (h) calculating a post-docking cornea apex location based on the pre-docking cornea apex location, the pre-docking pupil center location, and the post-docking pupil center location.

In another aspect, the present invention provides an ophthalmic laser system, which includes: a fixation light source configured to generate a fixation light which exits the ophthalmic laser system along an optical axis at a beam exit of the ophthalmic laser system; one or more docking illumination light sources configured to generate one or more docking illumination beams, each of the one or more docking illumination beams exiting the ophthalmic laser system in a direction which has a predefined spatial relationship with the optical axis of the ophthalmic laser system; a patient interface device coupled to the beam exit, having an optical window through which the fixation light and the one or more docking illumination beams pass; a camera configured to capture reflected light from an eye disposed below the patient interface device; a controller coupled to the camera, programmed to perform the following steps: (a) while the eye is positioned below the patient interface within a predefined distance range, the eye is looking through the patient interface device at the fixation light, and the one or more docking illumination beams are incident on the eye, controlling the camera to obtain a first image of the eye; (b) after the patient interface is coupled to the eye, controlling the camera to obtain a second image of the eye by the camera; (c) based on the first image, identifying positions of one or more light spots representing reflected light of the one or more docking illumination beams, and calculating a pre-docking cornea apex location based on the positions of the one or more light spots; (d) based on the first image, identifying a pupil of the eye and calculate a pre-docking pupil center location; (e) based on the second image, identifying a pupil of the eye and calculate a post-docking pupil center location; and (f) calculating a post-docking cornea apex location based on the pre-docking cornea apex location, the pre-docking pupil center location, and the post-docking pupil center location.

In preferred embodiments, the step of calculating the post-docking cornea apex location uses the following equation:

$$(XA', YA') = (\gamma * XA + XB' - \gamma * XB, \gamma * YA + YB' - \gamma * YB),$$

wherein (XA', YA') represents the post-docking cornea apex location, (XA, YA) represents the pre-docking cornea apex location, (XB, YB) represents the pre-docking pupil center location, (XB', YB') represents the post-docking pupil center location, and $\gamma$ is a magnification correction factor between the first and second images.

In preferred embodiments, the step of generating one or more docking illumination beams includes: generating two docking illumination beams, the two docking illumination beams being located within a plane that passes through the optical axis, at oblique angles relative to the optical axis, one on each side of and symmetrical with respect to the optical axis; and the step of calculating the pre-docking cornea apex location includes: identifying positions of two light spots representing reflected light of the two docking illumination beams, and calculating the pre-docking cornea apex location as a center of a line segment connecting the positions of the two light spots.

It is to be understood that both the foregoing general description and the following detailed description are exemplary and explanatory and are intended to provide further explanation of the invention as claimed.

BRIEF DESCRIPTION OF DRAWINGS

FIG. 2 schematically illustrates a method for locating the visual axis for a corneal lenticule procedure according to an embodiment of the present invention.

FIGS. 3A and 3B illustrate a single-piece patient interface device that may be used in embodiments of the present invention. FIG. 3B is a bottom view of the patient interface, showing a fixation light as it appears through the optical window of the patient interface.

FIGS. 5A-5D illustrates examples of images taken during the process of FIG. 2 according to an embodiment of the present invention.

DETAILED DESCRIPTION OF THE INVENTION

Embodiments of the present invention provide a method, during a corneal lenticule procedure, for finding the visual axis location before eye docking, to track the visual axis location displacement during docking, and to center the lenticule incision pattern at the visual axis location after docking, without ink-marking the visual axis location at the center of the cornea with ink or other substance. To ink-mark the visual axis at the cornea surface not only adds a step to the procedure, but also increases risk of introducing roughness to the cornea surface.

Here, docking refers to the process of coupling the patient's eye to the laser delivery head of the ophthalmic laser system via a patient interface device. The patient interface device mechanically and optically couples the eye to the laser system optics during the procedure.

Figure 1:
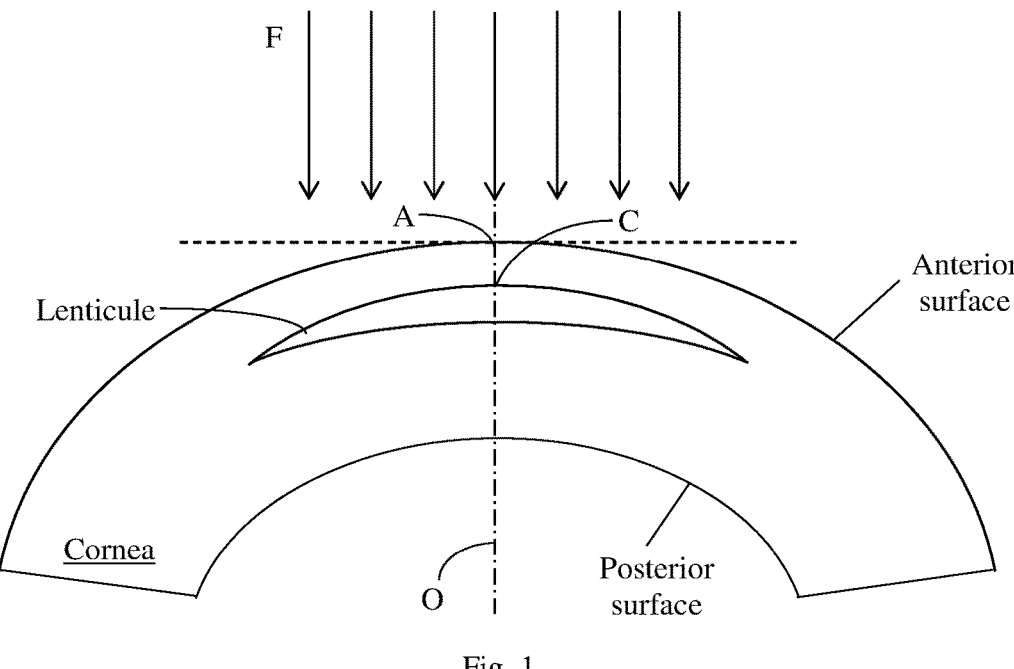
FIG. 1 schematically illustrates a lenticule within the cornea and its relation to the visual axis and fixation light in an ophthalmic corneal lenticule procedure according to embodiments of the present invention.

The eye optics has four refraction surfaces: anterior cornea surface, posterior cornea surface, anterior crystalline lens surface and posterior crystalline lens surface (as well as refraction due to gradient index of the crystalline lens). A corneal lenticule procedure treats the refraction of the anterior corneal surface. To best maintain the optical axis of the entire eye optics, the corneal lenticule should be centered at the optical axis of the anterior cornea surface. As shown in FIG. 1, when the eye is looking at a fixation light, the optical axis O of the anterior cornea surface is parallel to the direction of the fixation light beam F that normally crosses the anterior cornea surface at the cornea apex. The fixation light (sometimes referred to as the aim beam) is a collimated light beam generated by the ophthalmic laser system, traveling along the same optical path as the treatment laser beam at the beam exit (i.e. where the light beams exits the beam delivery head). It is typically used so that the patient can direct his eye to a target direction when instructed by the surgeon. Under this condition, as shown in FIG. 1, the cornea apex A is where the visual axis O crosses the cornea and is where the corneal lenticule center C should be aligned with.

Various techniques have been used in ophthalmic laser systems for corneal lenticule centration. One known method includes the following steps. Step 1: The patient looks at the fixation light of the ophthalmic laser system. Step 2: The normal reflection of the fixation light beam at the anterior cornea indicates the location of the apex of the cornea. This is the point the lenticule should be centered at. Step 3: The position of the bed that the patient is lying on is adjusted such that the cornea apex is at the center of the laser optical axis. The adjustment may be done manually by the surgeon, or automatically by the laser system. Step 4: The surgeon moves the bed up so that the eye is close to patient interface device that has been installed on the laser system. Step 5: The surgeon couples the patient interface to the eye. For example, the patient interface may be one that uses a suction ring to couple to the eye, and the surgeon activates a vacuum suction system to suction the patient interface onto the eye. Step 6: The lenticule incision is performed using the treatment laser beam, where the incision pattern is centered at the center of the patient interface which is also the optical axis of the laser system.

This technique has a problem that, if the cornea apex is not at the center of the patient interface, either due to it is originally not at the center or due to the apex being moved during suction, there is no centration adjustment after suction. This is one of the major issues of this conventional method.

Another known technique for corneal lenticule centration includes the following steps. Step 1: Before placing the patient interface, the surgeon asks the patient to look at the fixation light of a microscope that is separate from the ophthalmic laser system, and manually marks the cornea apex or pupil center using a corneal marking tool with corneal ink. Step 2: After coupling the patient interface to the eye (docking and applanation), the surgeon manually adjusts the lenticule incision pattern so it is centered at the central corneal mark. This is done by observing the image of the eye taken by a video camera of the laser system, determining the ink mark location, and moving the programmed incision pattern that the laser system is to execute so that it is centered on the ink mark. A disadvantage of this method is that it adds a step of corneal marking to the overall procedure, and it has the potential of introducing surface roughness or even damage to the visual field of the cornea.

Embodiments of the present invention provides a method, described below with reference to FIG. 2, for locating the visual axis of the cornea and centering the lenticule incision patterns accordingly, without marking the cornea with ink.

As shown in FIG. 2, in Step 1, a patient interface is coupled to the beam delivery head of the ophthalmic laser system, and ready to be coupled to the patient's eye. The patient interface is preferably a single-piece patient interface, i.e., one that is constructed as a integrated single-piece structure, an example of which is illustrated in FIGS. 3A (perspective view) and 3B (bottom view). As shown in FIGS. 3A-3B, the single-piece patient interface 30 has a cone shaped body with an upper end 31 configured to be coupled to the laser system's beam delivery head, and a lower end 32 configured to be coupled to the patient's eye, for example, by a suction ring 33 located at the lower end. The suction ring is a soft and flexible material forming a ring shaped suction channel, which can apply a suction force to the surface of the eye to secure the eye to the patient interface. The patient interface has a central optical window 34, covered by an applanation lens (also denoted by reference symbol 34), through which the various light beams from the laser system are delivered to the eye.

Some ophthalmic laser systems use a two-piece patient interface, i.e. a patient interface formed of a first piece configured to be coupled to the laser system beam delivery head, a second piece configured to be coupled to the eye (e.g. by a suction ring). The first and second pieces are separate pieces, which are coupled to each other as the last step of eye docking. The method described herein applies primarily to single-piece patient interfaces. Using a single-piece patient interface, the suction and applanation are done at the same time as the last step of docking; movement of the visual axis (cornea apex location) before and after suction and applanation is limited and can be effectively tracked by the method of the present embodiment. It should be noted, however, that if a two-piece patient interface is used but the two pieces are joined together before the lower piece is coupled to the eye, then the method described here is applicable, because the suction and applanation is the last step of docking.

Referring back to FIG. 2, in Step 2, the beam delivery head with the patient interface installed thereon is positioned to approximately align with the eye of the patient lying on the patient bed, and lowered close to but not yet in contact with the eye (e.g., leaving a distance of up to 75 mm, or more preferably up to 11 mm, between the lower surface of the applanation lens and the apex of the cornea). Alternatively, the beam delivery head may be lowered to a position where the applanation lens is just contacting and slightly pressing on the eye, for example, up to 0.6 mm below the unapplanated surface of the apex of the cornea. Within this preferred range, i.e. the distance between the applanation lens and the apex of the cornea being-0.6 mm to 11 mm, the light spots of the two docking illumination beams (described in more detail later) can be clearly seen. The positioning of the beam delivery head may be accomplished by moving the beam delivery head, and/or moving the patient bed. The surgeon then instructs the patient to look at the fixation light of the laser system through the patient interface. FIG. 3B is a bottom view of the patient interface, which illustrates the fixation light F as it appears to the patient (e.g. a red blinking dot). When the patient looks at the fixation light, which has a very narrow viewing angle, the visual axis of the eye is aligned with the fixation light and the optical axis of the laser system. Under this condition, the apex A of the cornea is where the visual axis O crosses the cornea and is where the center C of the corneal lenticule should be aligned with (see FIG. 1).

Figure 4:
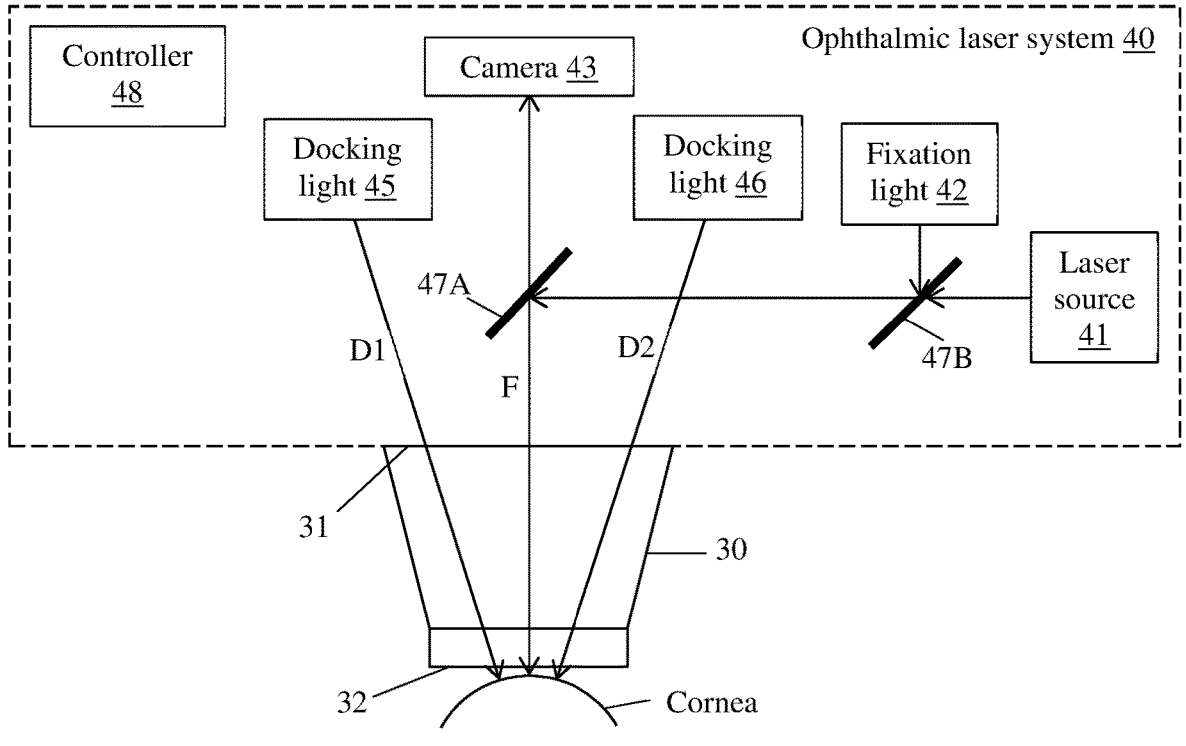
FIG. 4 schematically illustrates the relationship between the fixation light beam and two docking illumination light beams in an ophthalmic laser system according to an embodiment of the present invention.

In Step 3, two collimated docking illumination beams generated by the ophthalmic laser system are directed on the eye through the patient interface. As schematically illustrated in FIG. 4, the optical paths of the two docking illumination beams D1, D2 are located within a plane that passes through the optical axis of the laser system at the beam exit (which is also the optical path of the fixation light F), at oblique angles relative to the optical axis, one on each side of and symmetrical (i.e. same oblique angle) with respect to the optical axis. In FIG. 4, this plane is the plane of the drawing sheet. The two docking illumination beams D1 and D2 are generated by two docking illumination light sources 45 and 46 of the ophthalmic laser system 40.

As schematically illustrated in FIG. 4, the ophthalmic laser system 40 also includes a laser source 41 that generates the treatment laser beam, beam scanners or scanning assembly that scan the focal point of the treatment laser beam in transverse and depth directions (also represented by the box 41 in FIG. 4), a fixation light source 42 that generates the fixation light beam, and a camera 43 that receives reflected light from the eye to generate images of the eye. The laser system 40 further includes optical components that combine the optical paths of the treatment laser and the fixation light into a common optical path at the beam exit (labeled F in FIG. 4), and that separate the optical path of the reflected light traveling toward the camera 43 from that of the treatment laser and fixation light. In the example shown in FIG. 4, the optical components include two beamsplitters 47A and 47B, but other suitable beamsplitter arrangements and/or other suitable optical components may be used to achieve the above-described function. For example, beamsplitter 47B may alternatively be located above beamsplitter 47A to reflect the fixation light to the upper side of beamsplitter 47A. In another alternative configuration, the common optical path of the treatment laser and fixation light may be in a direction perpendicular to the drawing sheet, and the beamsplitter 47A is disposed in an orientation to reflect them toward the beam exit. Many other optical configurations are possible and are may be implemented by those of ordinary skill in the art.

Referring back to FIG. 2, Step 3 also includes taking a first image of the eye with the camera 43 when the patient is looking at the fixation light and when the two docking illumination beam are incident on the anterior cornea surface, by capturing the reflected light from the eye. This image will contain images of ocular structures such as the pupil and the iris, as well as two light spots which are the reflected light of the two docking illumination beams by the anterior cornea surface. From this image, the following information is obtained. First, the locations of the two reflected light spots of the docking illumination beams are measured, and the center of the line segment connecting the two light spots is calculated as the pre-docking cornea apex location (XA, YA). This is based on the fact that when the eye is looking at the fixation light, the cornea apex is aligned with the fixation light and the two incident points of the two docking illumination beams on the anterior cornea surface (which is a near spherical surface) are symmetrical on both sides of the cornea apex. Second, the pupil edge is fitted with a circle, and the center of the circle is calculated as the pre-docking pupil center location (XB, YB).

In Step 4, the beam delivery head is further lowered so that the applanation lens contacts the cornea surface (unless it is already lowered sufficiently to contact the cornea surface in Step 2), and the lower end of the patient interface 30 is coupled to the eye, such as by contacting the suction ring 32 with the eye and applying a suction to the suction ring. This accomplishes eye docking. The coupling of the suction ring to the eye causes the cornea to be applanated (flattened to an extent), and the cornea apex may be displaced due to asymmetry of suction pressure and/or asymmetry of the eye about the visual axis.

In Step 5, a second image of the eye is taken with the camera 43 after the suction and applanation. From the second image, the post-docking pupil center location (XB', YB') is calculated by fitting the pupil edge with a circle. The vector difference between the post-docking pupil center and the pre-docking pupil center, (XB'−XB, YB'−YB), is calculated as the displacement of cornea before and after docking. By adding this displacement to the pre-docking apex location (XA, YA), the post-docking apex location (XA', YA') is calculated as follows:

$$(XA', YA') = (\gamma * XA + XB' - \gamma * XB, \gamma * YA + YB' - \gamma * YB)$$

where $\gamma$ is a magnification correction factor between the pre- and post-docking (first and second) images. In some embodiments, $\gamma$ may be calculated in as follows: $\gamma = 0.0092 * H + 1$, where H is the distance (in mm) between the applanation lens surface and the cornea apex for the pre-docking image. H may be measured by any suitable measurement means within the beam delivery head and/or the patient interface device.

Note that all of the coordinates described here are in the camera's frame of reference.

In Step 6, with the patient's eye docked to the laser system, the laser system centers the lenticule incision pattern at the post-docking apex location (XA', YA'), and performs lenticule incisions according to the incision pattern. This includes generating a pulsed laser beam by the laser source 41, and scanning the focal point of the pulsed laser beam within the eye tissue using a scanning assembly of the laser system. The scanning assembly may include one or more of, for example, a resonant scanner, a scanline rotator, a fast Z scanner, a slow Z scanner, an XY scanner, etc.

FIGS. 5A-5D illustrate examples of the first and second images of a patient's eye taken in Step 3 and Step 5. FIG. 5A is a first image taken in Step 3, when the patient's eye is looking at the fixation light, with the two docking illumination beams illumining the eye, immediately before suction is applied to the patient interface. FIG. 5B is the same image as in FIG. 5A, but with annotations added to indicate various features in the image, including the reflections of the two docking illumination beams D1 and D2, the apex location (located at the center of the line segment connecting D1 and D2), the circle that fits the pupil, and the pupil center location. FIG. 5C is a second image taken in Step 5, after suction and applanation have occurred. Note that the docking illumination beams have been turned off. FIG. 5D is the same image as in FIG. 5C, but with annotations added to indicate various features in the image, including the circle that fits the pupil and the pupil center location. The small and large circles in FIGS. 5A and 5C (also in 5B and 5D) are reference circles that have fixed locations in the camera's frame of reference. Comparing FIGS. 5B and 5D, it can be seen that the pupil center has shifted after suction and applanation, as can be seen by comparing the pupil center locations relative to the small reference circle in FIGS. 5B and 5D.

In the system configuration in the embodiment of FIG. 4, two docking illumination beams are disposed coplanar with, and symmetrical with respect to, the optical axis of the laser system. In alternative embodiments, the two docking illumination beams may have other spatial relationships with the optical axis, or other numbers of docking illumination beam(s) may be employed with suitable spatial relationships with the optical axis.

For example, in one alternative embodiment (not shown in the drawings), only one docking illumination beam is employed, propagating in a direction coaxial with the optical axis of the laser system (and hence the fixation light). This may be accomplished, for example, using an additional beamsplitter to couple the docking illumination beam to the laser system optical axis. In this case, in the first eye image taken in Step 3, i.e. before suction is applied and when the patient is looking at the fixation light, the cornea apex position is the light spot of the reflected docking illumination beam. Thus, the calculation of the cornea apex location (XA, YA) in Step 3 is simplified. The other steps of the process of FIG. 2 remain the same, including the calculation in Step 5.

In another alternative embodiment (not shown in the drawings), the two docking illumination beams are coplanar with the optical axis but are not symmetrical with respect to the optical axis, although this alternative arrangement will complicate the calculation of the apex location based on the first image taken in Step 3. The other steps of the process of FIG. 2 remain the same, including the calculation in Step 5.

In another alternative embodiment (not shown in the drawings), three, four or more docking illumination beams are provided, located on a geometric cone around the optical axis (i.e. having the same oblique angles) and distributed evenly or unevenly around the optical axis. Such docking illumination beams will form three, four or more light spots in the first image taken in Step 3, distributed evenly or unevenly around a circle (if evenly, they form a regular polygon), and the cornea apex may be calculated as the center of the circle (or the regular polygon). The other steps of the process of FIG. 2 remain the same, including the calculation in Step 5.

In another alternative embodiment (not shown in the drawings), two pairs of docking illumination beams are provided, each pair being coplanar with the optical axis. The two planes of the two pairs of beams are not required to be perpendicular to each other. The oblique angles for the beams within each pair or between the two pairs are not required to be equal. Such docking illumination beams will form two pairs of light spots in the first image taken in Step 3, ant the cornea apex may be calculated as the intersection of two line segments that respectively connect the two pairs of spots. The other steps of the process of FIG. 2 remain the same, including the calculation in Step 5.

The various data processing steps described above, such as calculating the positions of the docking illumination light spots and calculating the cornea apex position in Step 3, the circle fitting in Steps 3 and 5, and calculating the vector difference and the post-docking cornea apex location in Step 5, may be performed by a programmed controller 48 which is a part of the ophthalmic laser system 40 (see FIG. 4). The controller 48 is also coupled to the various other components of the laser system 40 such as the laser source and beam scanners, and controls them to execute the incision patterns in Step 6.

An alternative method of centering the lenticule incision pattern, without marking the cornea, is to center the pattern at the pupil center. While pupil center is not exactly aligned with the visual axis of the cornea, it is close to it or it is close to the visual axis of the entire eye. Note that LASIK usually use pupil center instead of the cornea apex as centration target. This alternative method does not require the use of the two docking illumination lights or the calculations described above, except for fitting the pupil to a circle.

It should be noted that with the above-described cornea axis location method, peripheral corneal marks may still be needed for aligning the cylinder axis of the cornea if astigmatism treatment is desired. Marking peripheral corneal marks is less concerning as it is not done in the visual field. Alternatively, if an iris image is taken from a preop measurement (done at an measurement system independent of the ophthalmic laser system 40) and matched with an iris image taken by the camera 43 of the laser system 40, then the peripheral marking step may be eliminated as well, providing a corneal lenticule procedure that is entirely corneal-marking free.

The above-described method for locating the visual axis and cornea apex can be used for wavefront-guided corneal lenticule procedure, in which the shape of the lenticules are designed based on wavefront measurement of the eye and the designed amount of vision correction.

It will be apparent to those skilled in the art that various modification and variations can be made in the method and related apparatus of the present invention without departing from the spirit or scope of the invention. Thus, it is intended that the present invention cover modifications and variations that come within the scope of the appended claims and their equivalents.

The invention claimed is:

1. A method for locating a cornea apex of a patient's eye using an ophthalmic laser system, comprising:
    (a) coupling a patient interface device to the ophthalmic laser system;
    (b) positioning the patient's eye and the patient interface device relative to each other such that the eye is below the patient interface device within a predefined distance range, without coupling the patient interface to the eye;
    (c) generating a fixation light which exits the ophthalmic laser system along an optical axis of the ophthalmic laser system;
    (d) generating one or more docking illumination beams, each of the one or more docking illumination beams exiting the ophthalmic laser system in a direction which has a predefined spatial relationship with the optical axis of the ophthalmic laser system;
    (e) while the eye is not coupled to the patient interface device, the eye is looking through the patient interface device at the fixation light, and the one or more docking illumination beams are incident on the eye, obtaining a first image of the eye;
    (f) coupling the patient interface device to the eye;
    (g) obtaining a second image of the eye while the patient interface device is coupled to the eye;
    (h) based on the first image, identifying positions of one or more light spots representing reflected light of the one or more docking illumination beams, and calculating a pre-docking cornea apex location based on the positions of the one or more light spots;
    (i) based on the first image, identifying a pupil of the eye and calculating a pre-docking pupil center location;
    (j) based on the second image, identifying a pupil of the eye and calculating a post-docking pupil center location; and
    (k) calculating a post-docking cornea apex location based on the pre-docking cornea apex location, the pre-docking pupil center location, and the post-docking pupil center location.

2. The method of claim 1, wherein step (k) includes calculating the post-docking cornea apex location using:

$$(XA', YA') = (\gamma * XA + XB' - \gamma * XB, \gamma * YA + YB' - \gamma * YB),$$

wherein (XA', YA') represents the post-docking cornea apex location, (XA, YA) represents the pre-docking cornea apex location, (XB, YB) represents the pre-docking pupil center location, (XB',YB') represents the post-docking pupil center location, and γ is a magnification correction factor between the first and second images.

3. The method of claim 2, wherein the magnification correction factor between the first and second images, γ, is calculated by γ=0.0092*H+1, where His a distance in mm between an applanation lens surface of the patient interface device and the cornea apex when the first image is obtained.

4. The method of claim 1, wherein step (d) includes: by two docking illumination light sources, generating two docking illumination beams, the two docking illumination beams being located within a plane that passes through the optical axis, at oblique angles relative to the optical axis, one on each side of and symmetrical with respect to the optical axis; and wherein step (h) includes: identifying positions of two light spots representing reflected light of the two docking illumination beams, and calculating the pre-docking cornea apex location as a center of a line segment connecting the positions of the two light spots.

5. The method of claim 1, wherein step (d) includes: by a single illumination light source, generating a docking illumination beam which is coaxial with the optical axis; and wherein step (h) includes: identifying a position of a light spot representing reflected light of the docking illumination beam, and calculating the pre-docking cornea apex location as the position of the light spot.

6. The method of claim 1, wherein step (i) includes fitting the pupil in the first image to a first circle and calculating a center of the first circle as the pre-docking pupil center, and step (j) includes fitting the pupil in the second image to a second circle and calculating a center of the second circle as the post-docking pupil center.

7. A method implemented in an ophthalmic laser system for locating a cornea apex of a patient's eye, comprising:

(a) by a fixation light source of the ophthalmic laser system, generating a fixation light which exits the ophthalmic laser system along an optical axis of the ophthalmic laser system;

(b) by one or more docking illumination light sources of the ophthalmic laser system, generating one or more respective docking illumination beams, each of the one or more docking illumination beams exiting the ophthalmic laser system in a direction which has a predefined spatial relationship with the optical axis of the ophthalmic laser system;

(c) while a patient interface device is coupled to the ophthalmic laser system, the eye is positioned below the patient interface within a predefined distance range, the eye is looking through the patient interface device at the fixation light, and the one or more docking illumination beams are incident on the eye, obtaining a first image of the eye by a camera of the ophthalmic laser system;

(d) after the patient interface is coupled to the eye, obtaining a second image of the eye by the camera; and by a controller of the ophthalmic laser system:

(e) based on the first image, identifying positions of one or more light spots representing reflected light of the one or more docking illumination beams, and calculating a pre-docking cornea apex location based on the positions of the one or more light spots;

(f) based on the first image, identifying a pupil of the eye and calculating a pre-docking pupil center location;

(g) based on the second image, identifying a pupil of the eye and calculating a post-docking pupil center location; and (h) calculating a post-docking cornea apex location based on the pre-docking cornea apex location, the pre-docking pupil center location, and the post-docking pupil center location.

8. The method of claim 7, wherein step (h) includes calculating the post-docking cornea apex location using:

$$(XA', YA') = (\gamma * XA + XB' - \gamma * XB, \gamma * YA + YB' - \gamma * YB),$$

wherein (XA', YA') represents the post-docking cornea apex location, (XA, YA) represents the pre-docking cornea apex location, (XB, YB) represents the pre-docking pupil center location, (XB',YB') represents the post-docking pupil center location, and γ is a magnification correction factor between the first and second images.

9. The method of claim 8, wherein the magnification correction factor between the first and second images, γ, is calculated by γ=0.0092*H+1, where His a distance in mm between an applanation lens surface of the patient interface device and the cornea apex when the first image is obtained.

10. The method of claim 7, wherein step (b) includes: by two docking illumination light sources, generating two docking illumination beams, the two docking illumination beams being located within a plane that passes through the optical axis, at oblique angles relative to the optical axis, one on each side of and symmetrical with respect to the optical axis; and wherein step (e) includes: identifying positions of two light spots representing reflected light of the two docking illumination beams, and calculating the pre-docking cornea apex location as a center of a line segment connecting the positions of the two light spots.

11. The method of claim 7, wherein step (b) includes: by a single illumination light source, generating a docking illumination beam which is coaxial with the optical axis; and wherein step (e) includes: identifying a position of a light spot representing reflected light of the docking illumination beam, and calculating the pre-docking cornea apex location as the position of the light spot.

12. The method of claim 7, wherein step (f) includes fitting the pupil in the first image to a first circle and calculating a center of the first circle as the pre-docking pupil center, and step (g) includes fitting the pupil in the second image to a second circle and calculating a center of the second circle as the post-docking pupil center.

13. The method of claim 7, further comprising, by the controller:

defining a lenticule incision pattern centered at the post-docking apex location; and while the patient interface device is coupled to the eye, controlling a laser source and beam scanner assembly of the ophthalmic laser system to deliver a pulsed laser beam to the eye according to the lenticule incision pattern.

14. An ophthalmic laser system, comprising:

a fixation light source configured to generate a fixation light which exits the ophthalmic laser system along an optical axis at a beam exit of the ophthalmic laser system;

one or more docking illumination light sources configured to generate one or more docking illumination beams, each of the one or more docking illumination beams exiting the ophthalmic laser system in a direction which has a predefined spatial relationship with the optical axis of the ophthalmic laser system;

a patient interface device coupled to the beam exit, having an optical window through which the fixation light and the one or more docking illumination beams pass;

a camera configured to capture reflected light from an eye disposed below the patient interface device;

a controller coupled to the camera, programmed to perform the following steps:

(a) while the eye is positioned below the patient interface within a predefined distance range, the eye is looking through the patient interface device at the fixation light, and the one or more docking illumination beams are incident on the eye, controlling the camera to obtain a first image of the eye;

(b) after the patient interface is coupled to the eye, controlling the camera to obtain a second image of the eye by the camera;

(c) based on the first image, identifying positions of one or more light spots representing reflected light of the one or more docking illumination beams, and calculating a pre-docking cornea apex location based on the positions of the one or more light spots;

(d) based on the first image, identifying a pupil of the eye and calculate a pre-docking pupil center location;

(e) based on the second image, identifying a pupil of the eye and calculate a post-docking pupil center location; and (f) calculating a post-docking cornea apex location based on the pre-docking cornea apex location, the pre-docking pupil center location, and the post-docking pupil center location.

15. The system of claim 14, wherein step (f) includes calculating the post-docking cornea apex location using:

$$(XA', YA') = (\gamma * XA + XB' - \gamma * XB, \gamma * YA + YB' - \gamma * YB),$$

wherein (XA', YA') represents the post-docking cornea apex location, (XA, YA) represents the pre-docking cornea apex location, (XB, YB) represents the pre-docking pupil center location, (XB',YB') represents the post-docking pupil center location, and $\gamma$ is a magnification correction factor between the first and second images.

16. The system of claim 15, wherein the magnification correction factor between the first and second images, $\gamma$, is calculated by $\gamma=0.0092*H+1$, where H is a distance in mm between an applanation lens surface of the patient interface device and the cornea apex when the first image is obtained.

17. The system of claim 14, wherein the one or more docking illumination light sources include two docking illumination light sources, configured to generate two docking illumination beams, the two docking illumination beams being located within a plane that passes through the optical axis, at oblique angles relative to the optical axis, one on each side of and symmetrical with respect to the optical axis; and wherein step (c) includes: identifying positions of two light spots representing reflected light of the two docking illumination beams, and calculating the pre-docking cornea apex location as a center of a line segment connecting the positions of the two light spots.

18. The system of claim 14, wherein the one or more docking illumination light sources include a single illumination light source, configured to generate a docking illumination beam which is coaxial with the optical axis; and wherein step (c) includes: identifying a position of a light spot representing reflected light of the docking illumination beam, and calculating the pre-docking cornea apex location as the position of the light spot.

19. The system of claim 14, wherein step (d) includes fitting the pupil in the first image to a first circle and calculating a center of the first circle as the pre-docking pupil center, and step (e) includes fitting the pupil in the second image to a second circle and calculating a center of the second circle as the post-docking pupil center.

20. The system of claim 14, wherein the controller is further programmed to perform the following steps:

defining a lenticule incision pattern centered at the post-docking apex location; and while the patient interface device is coupled to the eye, controlling a laser source and beam scanner assembly of the ophthalmic laser system to deliver a pulsed laser beam to the eye according to the lenticule incision pattern.

\*   \*   \*   \*   \*